(12) United States Patent
Nakai et al.

(10) Patent No.: US 7,060,497 B2
(45) Date of Patent: Jun. 13, 2006

(54) ADENO-ASSOCIATED VIRAL VECTOR-BASED METHODS AND COMPOSITIONS FOR INTRODUCING AN EXPRESSION CASSETTE INTO A CELL

(75) Inventors: Hiroyuki Nakai, Redwood City, CA (US); Mark A. Kay, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 618 days.

(21) Appl. No.: 09/797,858

(22) Filed: Mar. 1, 2001

(65) Prior Publication Data

US 2002/0058341 A1    May 16, 2002

Related U.S. Application Data

(60) Provisional application No. 60/186,843, filed on Mar. 3, 2000.

(51) Int. Cl.
C12N 15/63 (2006.01)
C12N 15/00 (2006.01)
C12P 21/06 (2006.01)
A01N 63/00 (2006.01)
C07H 21/02 (2006.01)

(52) U.S. Cl. ............. 435/455; 435/456; 435/69.1; 435/320.1; 435/325; 424/93.2; 536/23.1

(58) Field of Classification Search ............. 435/172.1, 435/172.3, 235.1, 320.1, 325, 69.6, 366, 435/69.1, 367, 369; 514/44; 424/93.1, 93, 424/93.3; 536/23.1
See application file for complete search history.

(56) References Cited

U.S. PATENT DOCUMENTS

| 5,830,730 A | 11/1998 | German et al. |
| 5,843,742 A | 12/1998 | Natsoulis et al. |
| 5,952,221 A | 9/1999 | Kurtzman et al. |
| 5,989,540 A | 11/1999 | Carter et al. |
| 2003/0175974 A1 * | 9/2003 | Allen .................. 435/457 |

FOREIGN PATENT DOCUMENTS

WO    WO 99/60146    *   5/1999

OTHER PUBLICATIONS

AAV Helper-Free System, Instruction Manual, pp. 1-31.*
Kmiec, E.B. Gene Therapy. May-Jun., 1999. American Scientist, vol. 87, pp 240-247.*
Anderson, W.F, Human Gene Therapy. Apr., 1998. Nature, vol. 392, pp 25-30.*
Verma, I.M. and Somia, N. Gene Therapy-promises, problems and prospect. Sep., 1997. Nature, vol. 389, pp239-242.*
Meng R.D. and El-Deiry, W.S. Tumor Suppressor Genes as Targets for Cancer Gene Therapy. 1999. Gene Therapy of Cancer,Chapter 1. pp 3-18.*
Russell, S.J. Replicating Vectors for Gene Therapy of Cancer: Risks, Limitations and Prospects. 1994. European J. of Cancer vol. 30(A). pp 1165-1171.*
Yang et al, Concatamerization of Adeno-Associated Virus Circular Genomes Occurs through Intermolecular Recombination, Journal of Virology, Nov. 1999, vol. 73: 9468-9477.*
Mandel et al, Characterization of Intrastriatal Recombinant Adeno-Associated Virus-Mediated Gene transfer of Human Tyrosine Hydroxylase and Human GTP-Cyclohydrolase I in a Rat Model of Parkinson's Disease, J Neuroscience, 1998, vol. 18, No., 11, pp. 4271-4274.*
Bueler et al. (1999) "Adeno-Associated Viral Vectors for Gene Transfer and Gene Therapy." *Biol. Chem.*, vol. 380:613-622.
Burton et al. (1999) "Coexpression of factor VIII heavy and light chain adeno-associated viral vectors produces biologically active protein." *PNAS Online*, vol. 96(22):12725-12730.
Fan et al. (1998) "Behavioral Recovery in 6-Hydroxydopamine-Lesioned Rats by Cotransduction of Striatum with Tyrosine Hydroxylase and Aromatic L-Amino Acid Decarboxylase Genes Using Two Separate Adeno-Associated Virus Vectors." *Human Gene Therapy*, vol. 9:2527-2535.
Miao et al. (1998) "The kinetics of rAAV integration in the liver." *Nature Genetics*, vol. 19:13-15.

(Continued)

*Primary Examiner*—James Ketter
*Assistant Examiner*—Maria Marvich
(74) *Attorney, Agent, or Firm*—Bret E. Field; Bozicevic, Field & Francis, LLP (57) ABSTRACT

Methods and compositions are provided for introducing an expression cassette into a cell. In the subject methods, a population of at least two distinct adeno-associated viral particles is provided, where each distinct type of viral particle in the population comprises a different portion of the expression cassette to be introduced into the cell. The target cell is contacted with population of adeno-associated viral vectors under conditions sufficient to produce a hetero-concatemer in the cell, where the hetero-concatemer includes a functional expression cassette having an intron that includes an ITR sequence. Also provided by the subject invention are vector preparations for practicing the subject methods as well as kits for use in producing the vectors employed in the subject methods. The subject methods find use in a variety of different gene transfer applications, including both in vivo and in vitro gene transfer applications, and are particularly suited for use in the transfer of long genes.

18 Claims, 3 Drawing Sheets

OTHER PUBLICATIONS

Nakai et al. (2000) "Increasing the size of rAAV-mediated expression cassettes in vivo by intermolecular joining of two complementary vectors." *Nature Biotechnology*, vol. 18:527-532.

Patijn et al. (1999) "Hepatic Gene Therapy Using Adeno-associated Virus Vectors." *Seminars in Liver Disease*, vol. 19(1):61-69.

Rendahl et al. (1998) "Regulation of gene expression in vivo following transduction by two separate rAAV vectors." *Nature Biotechnology*, vol. 16:757-761.

Robbins et al. (1998) "Viral vectors for gene therapy." *TIBTECH*, vol. 16:35-40.

* cited by examiner

SEQUENCE LISTING

```
<160> NUMBER OF SEQ ID NOS: 5

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1 cttttcgca acgggtttgc cgccagaaca ca                                   32

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
gacagtatcg gcctcaggaa ga                                             22

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
cagtggcaaa gtggagattg tt                                             22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
tactccttgg aggccatgta gg                                             22

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
cgggaattca ctggccgtcg ttttacaacg                                     30
```

ADENO-ASSOCIATED VIRAL VECTOR-BASED METHODS AND COMPOSITIONS FOR INTRODUCING AN EXPRESSION CASSETTE INTO A CELL

CROSS REFERENCE TO RELATED APPLICATIONS

Pursuant to 35 U.S.C. § 119 (e), this application claims priority to the filing date of the U.S. Provisional Patent Application Ser. No. 60/186,843 filed Mar. 3, 2000, the disclosure of which is herein incorporated by reference.

ACKNOWLEDGEMENT OF GOVERNMENT SUPPORT

This invention was made with Government support under contract HL53682 awarded by the National Institutes of Health. The Government has certain rights in this invention.

INTRODUCTION

1. Field of the Invention

The field of this invention is gene therapy, particularly viral vector based gene therapy, and more particularly adeno-associated viral vector based gene therapy.

2. Background of the Invention

Recombinant adeno-associated virus (rAAV) vectors have great potential for use in clinical gene therapy. rAAV vectors are derived from a nonpathogenic parvovirus and provide a number of advantages over other viral vectors. First, rAAV viruses are capable of transducing nondividing cells. Second, they are capable of integrating into the host genome and providing long-term gene expression. In addition, they do not induce an immune response that eliminates the host cells. As such, rAAV vectors are believed to have a promising future in gene therapy.

A major shortcoming, however, of rAAV vectors is their limited packaging size, which restricts the vectors' use for some diseases that require a larger cDNA or regulatory element. Specifically, the package size limits the length of the non-viral DNA that may be present in the vector to about 4.7 kb. As such, rAAV vectors are not suited for use in applications where the transfer of long nucleic acids, e.g. large cDNAs, into a cell is required.

Accordingly, there is interest in the development of an rAAV vector-based method of gene transfer which is capable of transferring long nucleic acids, e.g. expression cassettes longer than about 4.7 kb, into a cell.

Relevant Literature

Adeno-associated viral vectors and their use in gene transfer applications are reviewed in: Hansruedi Biieler, Biol. Chem. (June 1999) 380:612–622; Robbins et al., TIBTECH (January 1998) 16:35–40; and Patjin & Kay, Semin. Liver. Dis. (1999) 19: 61–69. Other references of interest include: Burton, et al., Proc Natl Acad Sci USA (1999) 96: 12725–12730; Fan, et al., Hum. Gene Ther. (1998) 9: 2527–2535; Miao et al., Nat. Genet. (May 1998) 19: 13–15; Nakai et al., J. Virol. (July 1999) 73: 5438–5447; and Rendahl, et al., Nat Biotechnol (1998) 16, 757–761.

SUMMARY OF THE INVENTION

Methods and compositions are provided for introducing an expression cassette into a cell. In the subject methods, a population of at least two distinct adeno-associated viral particles is provided, where each distinct type of viral particle in the population comprises a different portion of the expression cassette to be introduced into the cell. The target cell is contacted with population of adeno-associated viral vectors under conditions sufficient to produce a hetero-concatemer in the cell, where the hetero-concatemer includes a functional expression cassette having an intron that includes an ITR sequence. Also provided by the subject invention are vector preparations for practicing the subject methods as well as kits for use in producing the vectors employed in the subject methods. The subject methods find use in a variety of different gene transfer applications, including both in vivo and in vitro gene transfer applications, and are particularly suited for use in the transfer of long expression cassettes into a cell.

DESCRIPTION OF THE SPECIFIC EMBODIMENTS

Methods and compositions are provided for introducing an expression cassette into a cell. In the subject methods, a population of at least two distinct adeno-associated viral particles is provided, where each distinct type of viral particle in the population comprises a different portion of the expression cassette to be introduced into the cell. The target cell is contacted with population of adeno-associated viral vectors under conditions sufficient to produce a hetero-concatemer in the cell, where the hetero-concatemer includes a functional expression cassette having an intron that includes an ITR sequence. Also provided by the subject invention are vector preparations for practicing the subject methods as well as kits for use in producing the vectors employed in the subject methods. The subject methods find use in a variety of different gene transfer applications, including both in vivo and in vitro gene transfer applications, and are particularly suited for use in the transfer of long expression cassettes. In further describing the subject invention, the subject methods are described first in greater detail, followed by a review of representative applications in which the subject methods find use, as well as vector preparations and kits for practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "and" and "the" include plural reference unless the context clearly dictates otherwise. Unless defined otherwise, all technical and scientific terms used herein have the same meaning as commonly understood to one of ordinary skill in the art to which this invention belongs.

Methods

As summarized above, the subject invention provides a method for introducing an expression cassette into a cell using a population, plurality or collection of at least two distinct adeno-associated viral vectors. By population or plurality of at least two distinct adeno-associated viral vectors is meant a population or collection or group in which at least two different types of adeno-associated viral vectors are present, where each distinct or different type of viral vector differs from the other type(s) of viral vector present in the population by having a different genomic sequence. As such, the genomic sequence of one type of viral vector in the population differs from the genomic sequence of any other type of viral vector present in the population. More specifically, the intra ITR domain of one type of viral vector differs in sequence from the intra ITR domain of any other type of viral vector present in the population. The number of different types of viral vectors present in the population is at least two and may be as high as four or higher, but generally does not exceed three and in many embodiments is two. As such, in many embodiments of the subject invention, the population of viral vectors that is employed is made up of two different types of viral vectors, i.e. a first type of viral vector and a second type of viral vector, where the first and second types of viral vectors differ from each other by genomic sequence. Generally, the two types of vectors differ from each other in their inter inverted terminal repeat (ITR) domains, i.e., in the domain flanked by the ITRs.

A feature of the subject methods is that the expression cassette that is to be introduced into the target or host cell by the subject methods is not delivered as one entity or piece of DNA into the cell, but is instead divided among the different types of adeno-associated viral vectors present in population that is employed in the method. In other words, the expression cassette is divided or split into different portions, where each different type of vector present in the population includes a different portion or piece of the divided or apportioned expression cassette in its genome, typically flanked between ITR sequences. For example, where the method involves the use of two distinct adeno associated viral vectors to introduce the expression cassette, the expression cassette is divided into a two different portions or pieces, i.e., a first portion and a second portion, where the first type of vector employed includes the first portion and the second type of vector employed includes the second portion.

For clarity of explanation, the subject methods are now described in terms of two vector embodiments, i.e. in terms of embodiments in which just two different types of adeno-associated viral vectors are employed. The following explanation should not be interpreted to limit the scope of the invention to two vector systems, as three or more vector systems are amenable to the subject methods, as indicated above.

The subject methods are suitable for use in the delivery of a broad range of different types of expression cassettes. In general, any type of expression cassette may be introduced into a cell so long as it is capable of being transcribed into mRNA when present in the cell as part of a hetero-concatemer in which the different portions of the expression cassette derived from the different types of vectors are separated by ITR sequence(s). Generally, the expression cassette will be one that includes an intron which provides for a convenient dividing site for the expression cassette. The intron is one that can be modified to include ITR sequences and not disrupt the transcription of the expression cassette into mRNA. In other words, the intron should be one that can include ITR sequence without disrupting the ability of the expression cassette to be transcribed into mRNA in the host cell.

Expression cassettes that are introduced or transferred into a cell by the subject methods generally include at least a promoter, an enhancer and a coding region, where these regions are well known to those of skill in the art. As is known to those of skill in the art, the above regions may be associated with each other in naturally occurring genomic sequences, or may be brought together from disparate sources via recombinant techniques to provide for specific characteristics, e.g. strong expression in the host cell, controllable expression in the host cell, tissue specific expression, etc.

In many embodiments, the expression cassettes delivered according to the subject methods are longer than those that can be delivered or transferred into a cell using a single adeno-associated vector. In these embodiments, the expression cassettes are longer than about 4.7 kb, and may be as long as 9 kb or longer. As such, in these embodiments the expression cassettes may range in length from about 5 to 20 kb, usually from about 5 to 10 kb.

In practicing the subject methods, the target or host cell (i.e. the cell into which the expression cassette is to be introduced) is contacted with the two or more different adeno associated viral vectors under conditions sufficient to produce a hetero-concatemer inside the target cell that includes a functional expression cassette, i.e. an expression cassette that is capable of being transcribed inside the host cell into an mRNA. Contact may be accomplished using any convenient protocol, where the target or host cell may be contacted with the different types of viral vectors sequentially or substantially simultaneously, if not at the same time, so long a hetero-concatemer as described above is produced in the cell following contact. The manner in which the cell is contacted with the vectors necessarily varies depending on whether the introduction of the expression cassette into the target cell is carried out in vitro or in vivo. Representative methods and conditions for contact are provided in the Experimental Section, infra.

Where introduction is to be carried out in vitro, any convenient in vitro protocol may be employed. For example, a culture of the target cell may be exposed to the viral vectors comprising the different portions of the expression cassette, e.g. by introducing the viral vectors into the culture medium. Suitable in vitro protocols are known to those of skill in the art.

Where introduction is to be carried out in vitro, contact is generally achieved by administering a suitable preparation of the viral vectors to the organism in which the target or host cell is located, e.g. to the multicellular organism. Any convenient mode of administration may be employed. In many embodiments, intravascular methods of administration are employed, e.g. intra-arterial, intravenous, etc., where intravenous administration is preferred in many embodiments.

As mentioned above, contact is carried out in a manner sufficient to produce a hetero-concatemer inside the host cell, where the intracellular hetero-concatemer includes the disparate portions of the expression cassette joined together such that a functional expression cassette is present in the cell, i.e. such that the expression cassette may be transcribed by the cellular elements into an mRNA. Because of the manner by which the hetero-concatemer is produced, each different portion of the expression cassette present therein that is contributed by a different vector is separated by a domain that includes ITR sequence. For example, in those embodiments where two different types of vectors are employed to separately introduce a first and second portion of an expression cassette into the host cell, the heteroconcatemer that is produced inside the host cell is one in which the first and second portions of the expression cassette are separated from each other by a domain that includes ITR sequence.

Utility

The subject methods find use in a variety of applications in which the introduction or transfer of a nucleic acid into a target cell, e.g. a therapeutic nucleic acid, is desired. In other words, the subject methods find use in applications of transducing a target cell with a nucleic acid. As such, the subject methods find use in gene therapy applications, including both in vitro and in vivo gene therapy applications. The subject vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides, and the like. The above list of proteins refers to mammalian proteins, and in many embodiments human proteins, where the nucleotide and amino acid sequences of the above proteins are generally known to those of skill in the art. Cancer therapeutic genes that may be delivered via the subject vectors include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

Applications in which the subject methods find use are also described in U.S. Pat. Nos. 5,989,540; 5,962,313; 5,952,221; 5,858,775; 5,858,351; 5,846,528; 5,843,742; 5,834,182; 5,789,390; 5,780,447; 5,589,377; 4,797,368; the disclosures of which are herein incorporated by reference.

The subject methods are particularly suited for use in the transduction of cells with long expression cassettes, where by long expression cassette is meant an expression cassette that is too long to be packaged into a single adeno associated viral particle. In other words, the subject methods are particularly suited for use in the introduction into a cell of expression cassettes that exceed about 4.7 kb in length, where the length of the expression cassette may be as long as 9 kb or longer.

Vector Preparations

Also provided by the subject invention are vector preparations for practicing the subject methods. The subject vector preparations are characterized by including a population of at least two distinct adeno-associated viral particles, where each distinct member of the population includes a portion of an expression cassette, as described above. The subject adeno-associated vector preparations may also include one or more additional components. Of particular interest in many embodiments are preparations that also include a pharmaceutical delivery vehicle. Delivery vehicles of interest include intravascular delivery vehicles, e.g. water for injection, saline, and the like.

Kits

Also provided are kits for use in preparing the subject vector preparations and using the prepared vector preparations to introduce a functional expression cassette into a cell, i.e., to transduce a cell with a functional expression cassette. The subject kits include at least a means for producing a population of at least two distinct adeno-associated viral particles, as described supra. The means for producing the population of at least two distinct adeno associated viral particles may vary depending on the particular vector preparation protocol to be employed, but in many embodiments will include a plasmid vector that includes an insertion site flanked by two ITR domains, where the insertion site includes a plurality of different restriction sites which may be exploited to introduce a portion of an expression cassette into the plasmid between the two ITR domains (i.e. an AAV vector plasmid). The vector production means may also include a source of Rep and/or Cap proteins, e.g. a plasmid vector that encodes these proteins (i.e. an AAV packaging plasmid). In addition, the subject means may include a source of adenovirus helper proteins, e.g. adenovirus, a plasmid containing genes encoding the requisite adenovirus helper proteins (i.e. an adenovirus helper plasmid), and the like. Finally, the kits may include an appropriate packaging cell line, e.g. 293 cell line, HeLa and the like, as well as the packaging cell lines described in U.S. Pat. Nos. 5,872,005; 5,837,484; 5,756,283; 5,691,176; and in vitro analogues thereof as described in U.S. Pat. No. 5,688,676; the disclosures of which are herein incorporated by reference. The various components of the kit may be present in separate containers or certain compatible components may be pre-combined into a single container, as desired. In addition, the kits will generally include instructions for practicing the subject methods, where the instructions may be present on one or more of: containers present in the kit, a package insert and the packaging of the kit.

The following examples are offered by way of illustration and not by way of limitation.

EXPERIMENTAL

I. Materials and Methods

A. Construction of rAAV Vectors and Plasmids.

All of the recombinant AAV vectors we used in this study were constructed based on AAV type 2. AAV-EF1α-nlsLacZ, AAV-Pless-nlsLacZ, AAV-EF1αEP, and AAV-(EF1αEP)$_2$ vectors were produced based on the following vector plasmids, pAAV-EF1α-nlsLacZ, pAAV-Pless-nlsLacZ, pAAV-EF1αEP, and pAAV-(EF1αEP)$_2$, respectively. To construct AAV-EF1α-nlsLacZ, a nuclear localizing signal (nls) was incorporated into the 5' end of the cytoplasmic E. coli β-galactosidase gene of pAAV-EF1α-LacZ by exchanging the 3.1-kb SalI/NdeI fragment of the cytoplasmic lacZ gene with the 3.0-kb NcoI/NdeI fragment of the nlslacZ gene from HR2PGKnlslacZ, which has an nls at the 5' end of the lacZ. pAAV-Pless-nlsLacZ was produced by removing a 0.9-kb 5' portion of the truncated EF1α enhancer/promoter including the TATA box, transcription initiation site, the splice donor of the exon 1, and most of intron 1, leaving a 0.2-kb 3' end of the EF1α-noncoding sequence including intron 1 and the splice acceptor of exon 2 of the EF1α gene.

The two enhancer/promoter rAAV vector plasmids, pAAV-EF1αEP and pAAV-(EF1αEP)$_2$ were constructed as follows. The human F.IX cDNA, poly A signal, and 0.2-kb 3' end of the EF1α enhancer/promoter downstream of the XhoI site in intron 1, were removed from pV4.1e-hF.IX (Nakai, H. et al. Adeno-associated viral vector-mediated gene transfer of human blood coagulation factor IX into mouse liver. *Blood* 91, 4600–4607 (1998)) with XhoI/BbrII double digestion. A 2.1-kb EF1α enhancer/promoter sequence upstream of the XhoI site in intron 1 was left between the two ITRs, making pITR-EF1αEP-ITR. A 12-bp XbaI/BamHI fragment at the multiple cloning sequence located between the 5' end of the EF1α enhancer/promoter and the 5' ITR was removed from pITR-EF1αEP-ITR by XbaI/BamHI double digestion and replaced with a XbaI-HincII-BamHI linker to make pITR-XHB-EF1αEP-ITR. A BglII/BsmI fragment of pASNori2 (Russell, D. W. & Hirata, R. K. Human gene targeting by viral vectors. *Nat Genet* 18, 325–330 (1998)) containing the SV40 enhancer was subcloned into a pBluescript KS—(Stratagene, La Jolla, Calif.)—based cloning plasmid and the BamHI/BglII fragment containing the transferred SV40 sequences was inserted into the unique BamHI site upstream of the EF1α enhancer/promoter, making pITR-XH-SV40E-EF1αEP-ITR or pAAV-EF1αEP. A 0.9 kb-XbaI/XhoI fragment of δEF1α enhancer/promoter was excised from pAAV-EF1α-LacZ, blunted, and then inserted into a unique HincII site of pITR-XH-SV40E-EF1αEP-ITR, in a head-to-head orientation relative to the other EF1α enhancer/promoter, producing pITR-δEF1αEP-SV40E-EF1αEP-ITR or pAAV-(EF1αEP)$_2$.

pEF1αEP-ITR-nlsLacZ was constructed as follows. A 2.3-kb XbaI/Sse 8387I fragment of pITR-EF1αEP-ITR, containing the EF1αEP and 3' ITR, was ligated to a 6.6-kb XhoI/XbaI fragment of pAAV-EF1α-LacZ, containing a 0.2-kb EF1αEP remnant downstream of the XhoI site in EF1α gene intron 1, the lacZ gene, SV40 poly A, 3' ITR, and 5' ITR, to make pEF1αEP-ITR-LacZ. This pEF1αEP-ITR-LacZ has an EF1αEP/cytoplasmic lacZ expression cassette with an ITR at the XhoI site in intron 1 of the EF1α gene, between two ITRs. The entire δEF1αEP of pAAV-EF1α-nlsLacZ was replaced with a δEF1αEP with an ITR in the intron 1 of pEF1αEP-ITR-LacZ, by exchanging the AgeI and SalI δEF1αEP fragments of pAAV-EF1α-nlsLacZ and pEF1αEP-ITR-LacZ, to make pEF1αEP-ITR-nlsLacZ. pBS-Pless-nlsLacZ was constructed by insertion of a NotI/NotI fragment of pAAV-Pless-nlsLacZ containing the whole Pless-nlslacZ cassette without ITRs, into a unique NotI site of pBluescript KS -.

Figure 1:
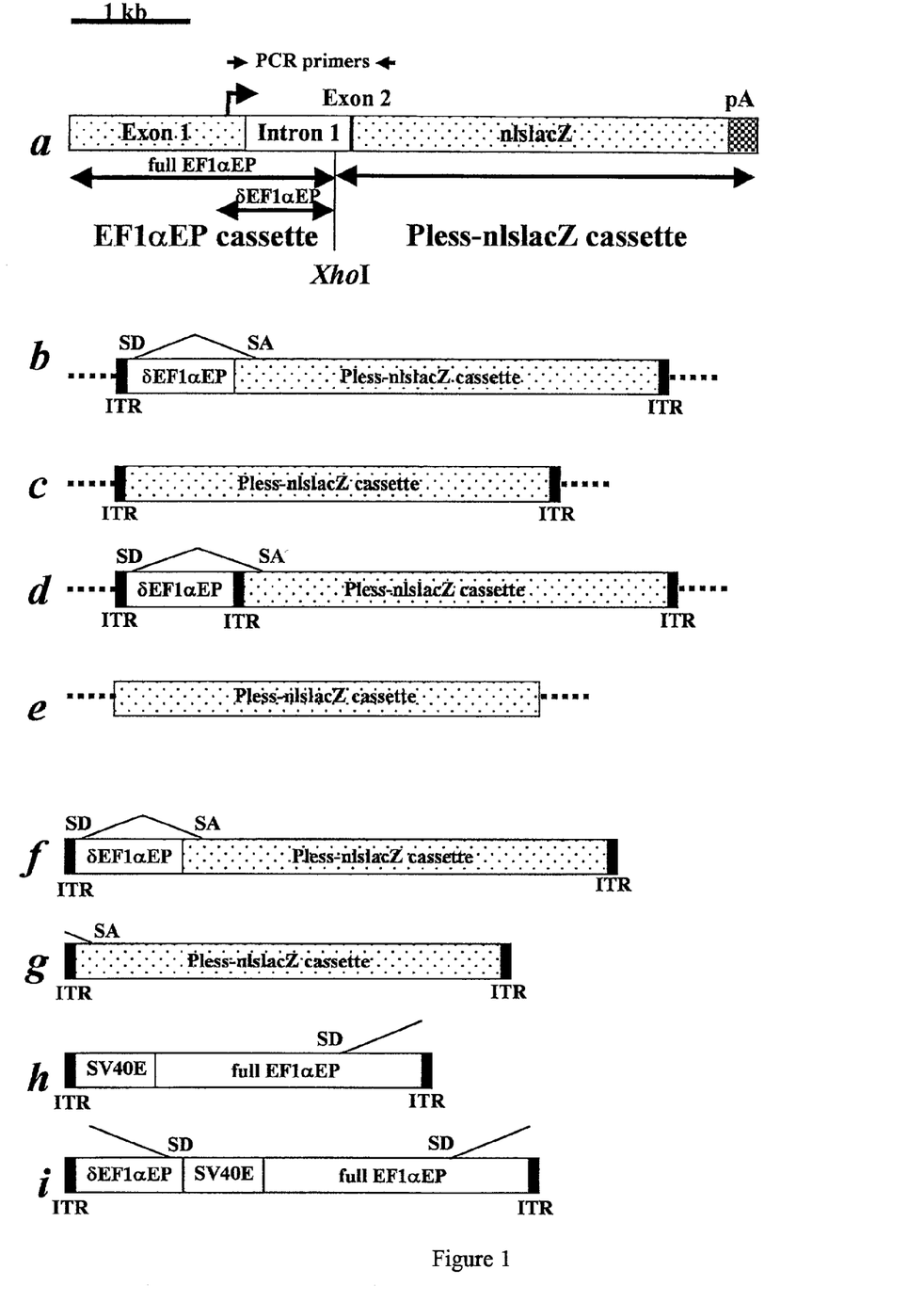
FIGS. 1a to 1i provide a schematic representation of the structures of the EF1αEP/nlslacZ expression cassette, nlslacZ plasmids, and rAAV vectors.

FIG. 1 provides a schematic representation of the structures of the EF1αEP/nlslacZ expression cassette, nlslacZ plasmids, and rAAV vectors. (a) The structure of the EF1αEP/nlslacZ cassette is shown. The EF1αEP/nlslacZ cassette comprises noncoding sequence of exons 1 and 2, and intron 1 of the human elongation factor 1α (EF1α) gene, followed by the *E. coli* lacZ gene with a nuclear localizing signal (nlslacZ). The EF1αEP/nlslacZ cassette was divided into two portions at the XhoI site in the EF1α gene intron 1, which were defined as the EF1αEP and Pless-nlslacZ cassettes. The EF1αEP cassette has exon 1 and most of intron 1 of the EF1α enhancer/promoter which includes the transcription initiation site, while the Pless-nlslacZ cassette has a 0.2-kb remnant of the EF1α enhancer/promoter, the nlslacZ gene and the poly A signal. Two kinds of the EF1αEPs, full EF1αEP and δEF1αEP (Nakai, H., Iwaki, Y., Kay, M. A. & Couto, L. B. Isolation of recombinant adeno-associated virus vector-cellular DNA junctions from mouse liver. *J Virol* 73, 5438–5447 (1999)) were used for this study. The transcription initiation site is indicated by an elbow arrow, and the primer locations to amplify the EF1αEP/nlslacZ transcripts (primers, EF1αP2and LacZP1) are shown by arrows. The structures of the plasmids, (b) pAAV-EF1α-nlsLacZ, (c) pAAV-Pless-nlsLacZ, (d) pEF1αEP-ITR-nlsLacZ, and (e) pBS-Pless-nlsLacZ. The dotted lines indicate the plasmid backbones. The splicing within the EF1αEP is shown by SD (splice donor) and SA (splice acceptor). The structures of rAAVs, (f) AAV-EF1α-nlsLacZ, (g) AAV-Pless-nlsLacZ, (h) AAV-EF1αEP, (i) AAV-(EF1αEP)$_2$. ITR, AAV inverted terminal repeat; pA, the SV40 early polyadenylation signal; SV40E, the SV40 enhancer.

All the rAAV vectors were prepared using the adenovirus-free triple plasmid transfection method (Matsushita, T. et al. Adeno-associated virus vectors can be efficiently produced without helper virus. *Gene Ther* 5, 938–945 (1998)) with pHLP19, an AAV helper plasmid that has been shown to make no recombinant wild-type AAV particles at a sensitively of 1 functional AAV virion in a background of $10^9$ rAAV particles (Matsushita, T., Godwin, S., Surosky, R. & Colosi, P. Improvements in AAV vector production: elimination of pseudo-wild type AAV. in *Second Annual Meeting of the American Society of Gene Therapy* p. 2a (Wash., D.C., 1999)). The vector purification procedure was outlined elsewhere (Burton, M. et al. Coexpression of factor VIII heavy and light chain adeno-associated viral vectors produces biologically active protein. *Proc Natl Acad Sci USA* 96, 12725–12730 (1999)). The physical vector titer was determined by a quantitative dot blot assay (Kessler, P. D. et al. Gene delivery to skeletal muscle results in sustained expression and systemic delivery of a therapeutic protein. *Proc Natl Acad Sci USA* 93, 14082–14087 (1996)).

B. In Vitro Transduction of 293 Cells with rAAV Plasmids 293 cells were maintained in Dulbecco's Modified Eagle Medium (Gibco BRL, Gaithersburg, Md.) supplemented with 10% fetal bovine serum (Hyclone, Logan, Utah) and penicillin-streptomycin (Gibco BRL), and seeded on 6 well plates at a density of 3.6×10$^5$/well. Twenty-four hours later, 293 cells were transfected with 2 μg of each plasmid by calcium phosphate method (Wigler, M. et al. Transformation of mammalian cells with an amplifiable dominant-acting gene. *Proc Natl Acad Sci USA* 77, 3567–3570 (1980)). The cells were harvested 36 hours after transfection for RNA and protein extraction. For Xgal staining, cells were trypsinized 32 hours after transfection and reseeded onto new 6 well plates with 5% of the total cells. The transduction efficiency was determined by Xgal staining 36 hours post-transfection. The protein analysis and Xgal staining was done in triplicate.

C. Animal Procedures

Six-week-old male C57B1/6 rag1 mice were obtained from Jackson Laboratory. All the animal experiments were performed according to the guidelines for animal care at Stanford University. The animals were anesthetized by inhalation of methoxyflurane (Metofane, Mallinckrodt Veterinary Inc., Mundelein, Ill.) and 200 μl of rAAV vector preparations were infused into the portal vein as previously described (Nakai, H. et al. Adeno-associated viral vector-mediated gene transfer of human blood coagulation factor IX into mouse liver. *Blood* 91, 4600–4607 (1998)). All the mice were sacrificed 6 weeks post-injection and liver samples were collected for protein, RNA, and histological analyses.

D. Histological Analysis

The mice were sacrificed 6 weeks post-injection, and liver samples were harvested. A piece from each four major liver lobes was embedded in O.C.T compound, and frozen on dry ice. Ten μm frozen sections were prepared, stained with Xgal as previously described (Kay, M. A. et al. Hepatic gene therapy: persistent expression of human alpha 1-antitrypsin in mice after direct gene delivery in vivo. *Hum Gene Ther* 3, 641–647 (1992)), and counterstained with hematoxylin. Approximately 500 hepatocyte nuclei were counted from each lobe with more than 2000 nuclei counted in total, and the hepatocyte transduction efficiency was calculated by dividing the number of Xgal positive nuclei by the total number of nuclei counted. Photomicroscopy was performed with Eclipse E800 (Nikon).

E. Protein Analysis

Expression levels of β-gal in transfected 293 cells and transduced mouse livers were determined by ELISA using a β-Gal ELISA Kit (Roche Molecular Biochemicals, Indianapolis, Ind.). Briefly, total protein was extracted from transfected 293 cells according to the manufacturer's recommendation, and extraction of cytoplasmic and nuclear protein from mouse livers was performed as previously described by Gorski et al. with a modification (Gorski, K., Carneiro, M. & Schibler, U. Tissue-specific in vitro transcription from the mouse albumin promoter. *Cell* 47, 767–776 (1986)). Total protein concentration in samples was measured based on the Lowry assay (Lowry, O. H., Rosebrough, N. J., Farr, A. L. & Randall, R. J. Protein measurement with the folin phenol reagent. *J Biol Chem* 193, 265–275 (1951)) using a DC Protein Assay kit (Bio-Rad, Hercules, Calif.) with bovine serum albumin as a standard. The results of β-gal ELISA were normalized with the total protein concentration.

F. RNA Analysis of the Liver Samples

One hundred-150 mg frozen mouse liver tissue was directly put into 1.5 ml of RNA STAT-60 reagent (Tel-Test "B", Friendswood, Tex.), homogenized with a motor-driven disposable plastic pestle, and total RNA was extracted according to the manufacturer's recommendation. For RT-PCR, total RNA was treated with DNase I (DNase I, amplification grade, Gibco BRL) at a concentration of 1 unit/μg total RNA at room temperature for 15 minutes, then incubated at 65° C. for 10 minutes in the presence of 2.3 mM EDTA to inactivate DNase I, and quickly chilled on ice. RT reaction was performed using a First-Strand cDNA Synthesis Kit (Amersham Pharmacia, Piscataway, N.J.) with random hexamers, and cDNA corresponding to 0.3 μg total RNA was used for the subsequent RT-PCR to amplify the EF1αEP/nlslacZ mRNA and murine glyceraldehyde 3-phosphate dehydrogenase (G3PDH) mRNA. The primers used for RT-PCR are given below.

EF1αP2: 5' CTTTTTCGCAACGGGTTTGCCGCCAGAACACA3' (SEQ ID NO:01)
LacZ P1: 5' GACAGTATCGGCCTCAGGAAGA 3' (SEQ ID NO:02)
mG3PDH P1: 5' CAGTGGCAAAGTGGAGATTGTT 3' (SEQ ID NO:03)
mG3PDH P2: 5' TACTCCTTGGAGGCCATGTAGG 3' (SEQ ID NO:04)

RT-PCR was carried out in the 50 μl PCR mixture containing 10 mM TrisHCl (pH 8.3), 50 mM KCl, 1.5 mM MgCl$_2$, 200 μM of each deoxynucleoside triphosphate, 0.4 μM each primer, and 2.5 units of Taq polymerase. The PCR cycle conditions were 95° C. for 2 min, followed by 30 cycles of 95° C. for 1 min, 58° C. for 30 sec and 72° C. for 30 sec for the amplification of EF1αEP/nlsklacZ mRNA, and 95° C. for 2 min, followed by 30 cycles of 95° C. for 1 min, 60° C. for 1 min, and 72° C. for 1 min for amplification of mG3PDH mRNA. Ten to 20 μl of each PCR reaction mixture was separated on a 1.5% agarose gel, and the bands were visualized with ethidium bromide staining. The EF1αEP/nlslacZ RT-PCR products were then transferred to a Duralon UV membrane (Stratagene, La Jolla, Calif.) and hybridized with a $^{32}$P-labeled lacZ specific oligonucleotide probe:
5' CGGGAATTCACTGGCCGTCGTTTTACAACG3' (SEQ ID NO:05).

The signals were detected by a Molecular Imager System (BioRad, Hercules, Calif.). The positive control plasmid for EF1αEP/nlslacZ RT-PCR, pCR2.1EF1αEP/nlslacZ, was constructed by inserting the RT-PCR product into plasmid pCR2.1, using an Original TA Cloning Kit (Invitrogen, Carlsbad, Calif.). RT-PCR positive controls were generated as follows. A known amount of pCR2.1EF1αEP/nlslacZ (i.e., 500, 50, 5, and 0.5 pg) was spiked into a RT-PCR reaction mixture containing RT product from 0.3 μg of total RNA from naïve mouse liver, and PCR cycles were carried out as described. Some RNA samples were subjected to RT-PCR after dilution with total RNA from naïve mouse liver to keep the total amount of RNA per tube constant.

Northern blot analysis (Sambrook, J., Fritsch, E. F. & Maniatis, T. *Molecular cloning: a laboratory manual*, (Cold Spring Harbor Laboratory, Cold Spring Harbor, N.Y., (1989)) using 10 μg of total RNA from 293 cells, or 20 μg of total RNA from mouse liver. Total RNA was denatured, separated on a 1.0% formamide gel, transferred to a Duralon UV membrane, hybridized with a $^{32}$P-labeled 2.3 kb-lacZ/SV40 poly A probe, and autoradiographed at −80° C.

II. Results

A. Incorporation of the AAV Inverted Terminal Repeat (ITR) Sequence into an Intron Does Not Affect the Correct Splicing of mRNA or Transgene Expression.

To test the feasibility of using two vectors to produce a single expression cassette and express a transgene product from a heterodimeric rAAV genome in mouse hepatocytes, different expression sequences that utilized the EF1αEP/nlslacZ cassette (human elongation 1α gene enhancer/promoter (EF1αEP)-lacZ with a nuclear localizing signal (nlslacZ) cassette) (FIG. 1a) were constructed. This cassette has a 0.9-kb intron contained within the EF1αEP, which is spliced out from the final mRNA transcript. This enhancer/promoter has been shown to work efficiently in mouse liver (Nakai, H. et al. Adeno-associated viral vector-mediated gene transfer of human blood coagulation factor IX into mouse liver. *Blood* 91, 4600–4607 (1998)). The EF1αEP/nlslacZ cassette was divided at the Xho I site into two portions within the intronic sequences and were identified as EF1αEP and Pless-nlslacZ (FIG. 1a). If these two portions of the expression cassette are incorporated in cis by heteroconcatemerization from two different rAAV constructs reconstituting a complete EF1αEP/nlslacZ cassette, the ITR sequences would be present in the intron at the XhoI site of this expression cassette (see FIG. 1a).

We used plasmid transfection assays to determine whether or not the ITR sequences within the intron would result in impaired processing of EF1α/nlslacZ mRNA or inefficient translation of β-galactosidase (β-gal). We constructed a plasmid, pEF1αEP-ITR-nlsLacZ, which has one ITR at the XhoI site in intron 1 of the EF1α gene, to mimic the heterodimer of two rAAV vectors reconstituting the complete EF1αEP/nlslacZ expression cassette (FIG. 1d), and compared the mRNA and protein expression in vitro to that of pAAV-EF1α-nlsLacZ, pAAV-Pless-nlsLacZ, and pBS-Pless-nlsLacZ (FIG. 1b, c and e). pAAV-EF1α-nlsLacZ has a complete EF1αEP/nlslacZ expression cassette between the two ITRs; pAAV-Pless-nlsLacZ lacks the EF1αEP sequences upstream of the XhoI site of intron 1, but has two ITRs; pBS-Pless-nlsLacZ has the Pless-nlslacZ cassette but lacks the two ITRs.

Figure 2:
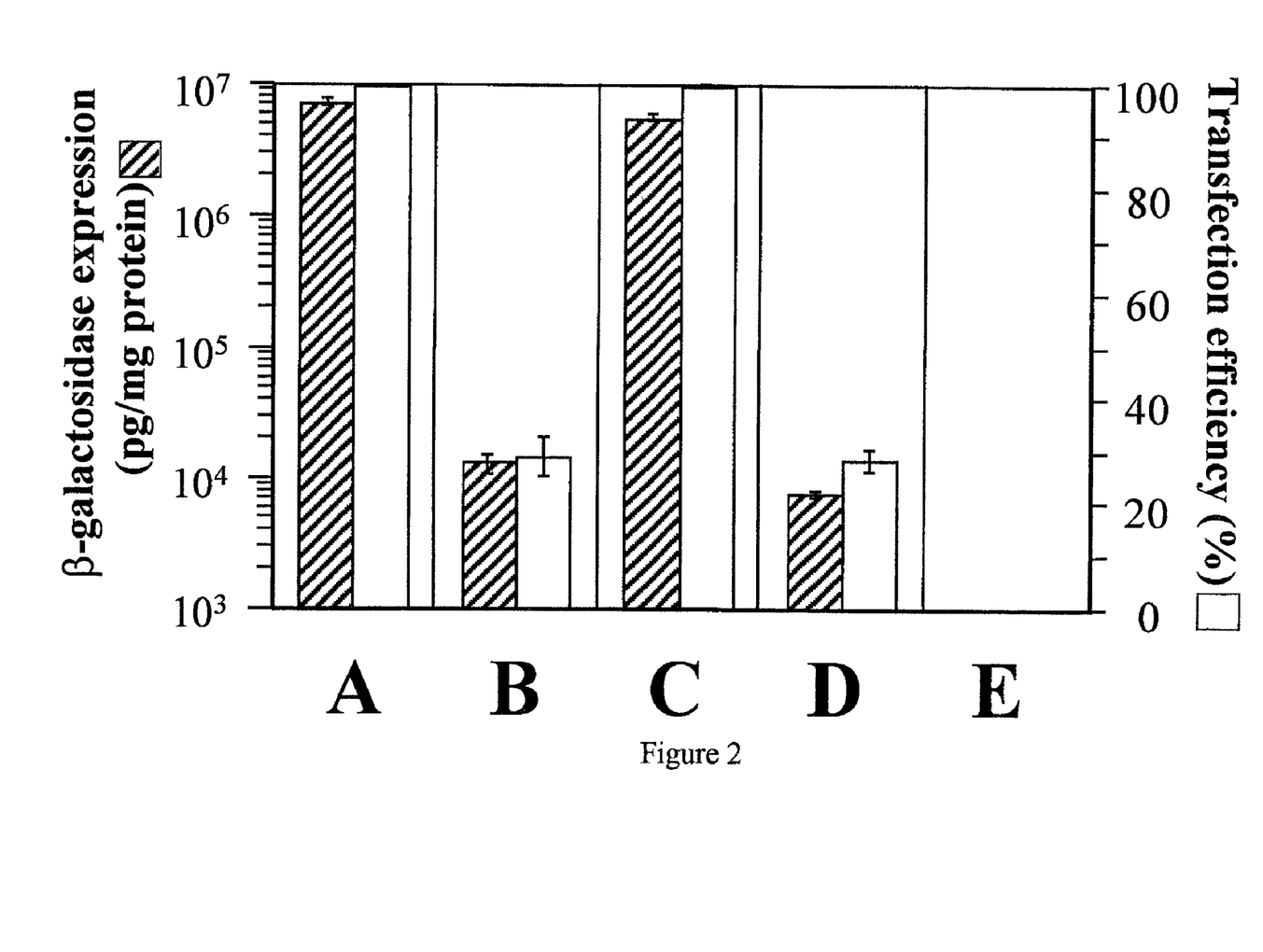
FIG. 2 provides a graphical representation of the results of transfection of 293 cells by the nlslacZ plasmids of the subject invention.

FIG. 2 shows the results of results of transfection of 293 cells by the above describes nlslacZ plasmids. (a) Transduction efficiency (gray bars) and β-gal expression (black bars) in 293 cells transfected with the nlslacZ plasmids. 293 cells were seeded on 6 well plates at a density of $3.6 \times 10^5$ cells per well, transfected with 2 μg of each plasmid, and the transduction efficiency and quantitation of β-gal protein were determined by Xgal staining and β-gal ELISA, respectively. The experiments were done in triplicate and the mean values are shown with error bars. The plasmids used were: (A) pAAV-EF1α-nlsLacZ, (B) pAAV-Pless-nlsLacZ, (C) pEF1αEP-ITR-nlsLacZ, (D) pBS-Pless-nlsLacZ, (E) pBluescript II KS—. (b) Northern blot analysis of 293 cells transfected with nlslacZ plasmids. Ten μg of total RNA was gel-separated, transferred to a nylon membrane, and hybridized with a lacZ/SV40 poly A probe. Lanes 1 to 5 are pAAV-EF1α-nlsLacZ, pAAV-Pless-nlsLacZ, pEF1αEP-ITR-nlsLacZ, pBS-Pless-nlsLacZ, and pBluescript II KS—transfected 293 cells, respectively. Lane 6, naïve 293 cells. The left upper panel shows a 3.3-kb EF1αEP/nlslacZ transcript. An nlslacZ mRNA of 3.5 kb was detected in an overexposed blot (left lower panel). Ethidium bromide-stained gel showing RNA integrity (right panel). M, a 0.24–9.5 kb RNA ladder (Gibco BRL).

More specifically, each plasmid was transfected into 293 cells and 36 hours later β-gal expression was assessed by determining the transfection efficiency and the quantity of β-gal protein (FIG. 2). The β-gal mRNA was also analyzed by Northern blot and Reverse Transcriptase-Polymerase Chain Reaction (RT-PCR). As shown in FIG. 2, there was no significant difference in transgene mRNA or protein expression between pAAV-EF1α-nlsLacZ and pEF1αEP-ITR-nlsLacZ transfected cells. The mRNA was correctly processed regardless of the presence of an ITR sequence in the intron (data now shown). When the enhancer and promoter region of the EF1αEP upstream of the XhoI site in intron 1 was removed, producing a Pless-nlslacZ cassette, β-gal expression dropped by about 500 fold, yet there was only a 3-fold drop in the number of lacZ positive cells (FIG. 2). This suggested that the addition of an enhancer/promoter increased the number of transgene specific mRNAs in each transfected cell. The low levels of β-gal protein expression from pAAV-Pless-nlsLacZ was presumed to come from a small amount of a second nlslacZ mRNA detected by Northern blot analysis. The second mRNA was ~0.2 kb longer than expected from EF1αEP-driven transcripts, and was also observed in 293 cells transfected with pBS-Pless-nlsLacZ. The identity of the longer mRNA was confirmed by RT-PCR studies using different primer pairs suggesting that the origin of the longer mRNA resulted from a cryptic transcription initiation site on the EF1αEP remnant in the Pless-nlslacZ cassette and not from the ITR or an aberrantly spliced transcript (data not shown).

B. Enhancement of Transgene Expression from a Promoter-less nlslacZ rAAV Vector by Co-injection of an Enhancer/Promoter rAAV Vector.

The ability to obtain functional mRNAs correctly spliced within an expression cassette split by an AAV-ITR allowed us to pursue a two-vector approach in vivo. We constructed a promoter-less rAAV, AAV-Pless-nlsLacZ, and two complementing vectors that contain the EF1α enhancer/promoter, AAV-EF1αEP and AAV-(EF1αEP)$_2$ (see FIG. 1g, h and i). The AAV-Pless-nlsLacZ contains the 3' remnant of the EF1α enhancer/promoter downstream of the XhoI site in intron 1 (0.2 kb), the lacZ gene with a nuclear localizing signal (nls), and the SV40 early polyadenylation (poly A) signal. The AAV-EF1αEP has the EF1α enhancer/promoter upstream of the XhoI site (2.2 kb) with a transcriptional orientation towards the ITR, and a fragment containing the SV40 enhancer. The AAV-(EF1αEP)$_2$ has two EF1α enhancer/promoters, which were placed in a head-to-head orientation with the SV40 enhancer between them. One EF1α enhancer/promoter was truncated by 1.3 kb (δEF1αEP) (Nakai, H., Iwaki, Y., Kay, M. A. & Couto, L. B. Isolation of recombinant adeno-associated virus vector-cellular DNA junctions from mouse liver. J Virol 73, 5438–5447 (1999)) because of the size limitation of rAAV packaging. The truncation of the EF1αEP did not affect the enhancer/promoter activity of the EF1αEP (data not shown). A single vector, or two vectors (FIG. 1f, g, h and i), were injected at a dose of $2.4 \times 10^{11}$ particles per vector in individual mice via portal vein, into 6 week-old C57B1/6 rag1 mice: Group 1, AAV-Pless-nlsLacZ only, n=3; Group 2, AAV-EF1αEP only, n=3; Group 3, AAV-(EF1αEP)$_2$ only, n=3; Group 4, AAV-Pless-nlsLacZ+AAV-EF1αEP, n=2; Group 5, AAV-Pless-nlsLacZ+AAV-(EF1αEP)$_2$, n=4; Group 6, controls, AAV-EF1α-nlsLacZ, n=3. All mice were sacrificed 6 weeks after vector administration. Hepatocyte transduction efficiency was assessed by determining the proportion of Xgal-stained hepatocytes in liver sections (Table 1), and the total amount of β-gal analyzed by ELISA from liver extracts (Table 1).

TABLE 1

Efficiency of hepatocyte transduction and β-galactosidase expression in mouse hepatocytes following rAAV administration.

| | | Transduction efficiency* (%) and β-galactosidase expression** (pg/mg protein) | | | | | |
|---|---|---|---|---|---|---|---|
| | | Mouse | | | | | Relative |
| | | 1 | 2 | 3 | 4 | Mean ± SD | transduction*** |
| G1: | AAV-Pless-nlsLacZ | 0.5 (47) | 0.6 (68) | 0.3 (40) | — | 0.5 ± 0.1 (52 ± 12) | 0.09 (0.07) |

TABLE 1-continued

Efficiency of hepatocyte transduction and β-galactosidase expression in mouse hepatocytes following rAAV administration.

| | | Transduction efficiency* (%) and β-galactosidase expression** (pg/mg protein) | | | | | Relative |
|---|---|---|---|---|---|---|---|
| | | Mouse | | | | | |
| | | 1 | 2 | 3 | 4 | Mean ± SD | transduction*** |
| G2: | AAV-EF1αEP | 0.0 | 0.0 | 0.0 | — | 0.0 | NA |
| | | (<1) | (<1) | (<1) | | (<1) | |
| G3: | AAV-(EF1αEP)2 | 0.0 | 0.0 | 0.0 | — | 0.0 | NA |
| | | (<1) | (<1) | (<1) | | (<1) | |
| G4: | AAV-Pless-nlsLacZ | 2.8 | 2.9 | — | — | 2.9 | 0.50 |
| | AAV-EF1αEP | (263) | (208) | | | (236) | (0.31) |
| G5: | AAV-Pless-nlsLacZ | 5.0 | 3.9 | 3.9 | 3.2 | 4.0 ± 0.6 | 0.69 |
| | AAV-(EF1αEP)2 | (246) | (676) | (419) | (450) | (448 ± 153) | (0.59) |
| G6: | AAV-EF1α-nlsLacZ | 5.2 | 5.6 | 6.6 | — | 5.8 ± 0.6 | 1.00 |
| | | (1072) | (564) | (656) | | (764 ± 221) | (1.00) |

*Xgal-positive nuclei/total nuclei counted (%)
**β-galactosidase antigen levels in liver extracts were normalized by total protein in samples (pg/mg protein), and shown in parentheses.
***Relative transduction efficiency and β-galactosidase expression (shown in parenthesis) as compared to Group 6 (G6)
SD, standard deviation; NA, not applicable.

Transduction efficiency was defined as the number of cells that express detectable levels of the transgene product rather than the number of cells that contains stable double-stranded vector genomes. While the number of transduced cells gives an indication of the frequency of cells that contain heteroconcatemers, it does not estimate the relative frequency that they form in vivo. Thus, we measured both the transduction efficiencies and total amount of transgene product when comparing each set of vectors (summarized in Table 1). No β-gal protein or transduced cells were observed in animals that received only the EF1αEP rAAV vectors (Groups 2 and 3). AAV-Pless-nlsLacZ-injected mice showed a low frequency of transduction at 0.5±0.1% and low β-gal expression (52±12 pg/mg protein), presumably due to weak promoter activity of the ITR sequences (Flotte, T. R. et al. Expression of the cystic fibrosis transmembrane conductance regulator from a novel adeno-associated virus promoter. *J Biol Chem* 268, 3781–3790 (1993)), or minimum promoter activity of an EF1αEP remnant (Kim, D. W., Uetsuki, T., Kaziro, Y., Yamaguchi, N. & Sugano, S. Use of the human elongation factor 1 alpha promoter as a versatile and efficient expression system. *Gene* 91, 217–223 (1990)). When the AAV-Pless-nlsLacZ and AAV-EF1αEP vectors were coinjected, liver transduction and β-gal expression was increased to 2.9% and 236 pg/mg protein, respectively. Furthermore, when AAV-Pless-nlsLacZ was coninjected with AAV-(EF1αEP)$_2$, hepatocyte transduction and β-gal expression was restored to about 60–70% of the AAV-EF1α-nlsLacZ-injected control mice (4.0±0.6% and 448±153 pg/mg protein versus 5.8±0.6% and 764±221 pg/mg protein, respectively. When we compared the transduction efficiency and β-gal expression between the three mice injected with the promoter-less vector (Group 1), and the six mice co-injected with the promoter-less and an enhancer/promoter vector (Groups 4 and 5), a Mann-Whitney U-test revealed a statistically significant difference (p<0.025). A summary of the transduction efficiencies and β-gal expression is shown in Table 1. The amount of β-gal protein in transduced livers measured by β-gal ELISA paralleled the transduction efficiencies or the number of the Xgal-positive hepatocytes (Table 1). These observations demonstrate that transgene expression in liver from a promoter-less rAAV vector can be significantly enhanced by a second vector with an enhancer/promoter, reaching up to 60–70% levels of that obtainable by a single, complete rAAV expression cassette.

C. The Mechanism of the Enhanced Gene Expression from Two Vectors.

Recent studies have demonstrated that heteroconcatemers are formed in mouse hepatocytes after intraportal administration of two rAAV vectors (Miao, C. H. et al. Non-random transduction of recombinant adeno-associated viral vectors in mouse hepatocytes in vivo: cell cycling does not influence hepatocyte transduction. *J. Virol* (in press), and Nakai et al., manuscript submitted), hence we reasoned that a heterodimer consisting of AAV-Pless-LacZ and an EF1αEP rAAV should reconstitute the complete EF1αEP/nlslacZ expression cassette allowing for correct transcription and mRNA processing, and ultimately β-gal gene expression in mouse hepatocytes. To demonstrate this, total RNA was extracted from the transduced mouse livers, and EF1αEP/nlslacZ transcripts were analyzed by RT-PCR. Similar to the studies performed in the cultured cells, the PCR primers were designed to detect mRNA transcripts that originated from the proper transcriptional initiation site. EF1αEP/nlslacZ mRNA transcripts were not detected in liver from animals injected with AAV-Pless-nlsLacZ only (Group 1), while the expected RT-PCR fragments were observed in the livers of mice co-injected with AAV-Pless-nlsLacZ and AAV-EF1αEP (Group 4) (data not shown). Even greater amounts of the cis-spliced mRNAs were found when AAV-(EF1αEP)$_2$ was used in place of AAV-EF1αEP (Group 5). These findings demonstrate that a single expression cassette divided into two rAAV vectors can be reconstituted by intermolecular ligation, and mRNA can be correctly processed if the vectors are designed to have the ITR sequences between the vectors spliced out from the mRNA.

However, as determined by the RT-PCR analysis, the relative amount of cis-spliced mRNA was not sufficient to explain the restoration of β-gal protein expression. To further pursue this we performed Northern blot analyses. Similar to what was found in the tissue culture studies, in mice that received two vectors, there were two nlslacZ mRNA transcripts that varied in size by about 0.2-kb. The predominate species in the AAV-EF1α-nlsLacZ vector-injected mice was the 3.3-kb transcript, while in the AAV-Pless-nlsLacZ-treated mice there was only a 3.5-kb mRNA transcript. The hepatic expression of this larger nlslacZ mRNA from AAV-Pless-nlsLacZ was further enhanced when mice were coinjected with an enhancer/promoter vector. Taken together, enhancement of transgene expression in mice injected with two vectors was the result of both the expected cis-spliced EF1αEP/nlsLacZ mRNAs transcribed from a heterodimer and cis-enhancement of the nlslacZ mRNA transcription in the Pless-nlslacZ cassette by EF1αEP vectors. The model explaining the mechanism(s) for enhanced gene expression is summarized in FIG. 3 as follows: (a) Uni-directional transcription from the EF1α enhancer/promoter in an AAV-EF1αEP/AAV-Pless-nlsLacZ heterodimer. (b) Bi-directional transcription from AAV-(EF1αEP)$_2$ in an AAV-Pless-nlsLacZ/AAV-(EF1αEP)$_2$/AAV-Pless-nlsLacZ heterotrimer. (c) Orientation independent cis-enhancement of the larger, 3.5-kb nlslacZ mRNA expression by AAV-EF1αEP. (d) Cis-enhancement of the larger nlslacZ mRNA by AAV-(EF1αEP)$_2$. Because the vector sequences flanking the ITRs are frequently deleted[11], cis-splicing may not necessarily work in an AAV-(EF1αEP)$_2$/AAV-Pless-nlsLacZ heterodimer. In this case, AAV-(EF1αEP)$_2$ may work as a cis-enhancer of the larger nlslacZ mRNA. The black boxes indicate the ITRs.

III. Discussion

We analyzed the transduction efficiency of a promoterless rAAV in hepatocytes and total β-gal expression in liver, with and without a second vector that contained the enhancer/promoter(s). We designed these two vectors so that they could reconstitute the complete expression cassette when they formed a heterodimer in a correct orientation.

When the AAV-Pless-nlsLacZ vector was co-injected with AAV-EF1αEP or AAV-(EF1αEP)$_2$ vector, liver transduction and β-gal expression were restored up to a maximum of 60–70% of the control vector that contained the complete EF1αEP/nlslacZ cassette. In a previous study, we mixed two vectors and performed two color-probe FISH analysis, demonstrating that stable rAAV heteroconcatemers were present in about 40% of the hepatocytes containing stable vector genomes (Miao, C. H. et al. Non-random transduction of recombinant adeno-associated viral vectors in mouse hepatocytes in vivo: cell cycling does not influence hepatocyte transduction. *J. Virol* (in press)). While this method did not measure the number of hepatocytes that were able to express two transgene products, the 40% value was close to the 50% to 70% relative efficiency of transduction detected by restoration of βgal expression using two split vectors compared to one complete vector. Some of the quantitative variations may also be due to differences in the detection limits using FISH and Xgal staining.

The restoration of β-gal protein expression here was higher than expected based on a statistical calculation of the probability for two rAAV vectors to link in a correct orientation. If dimer formation and linking orientation are random events, the probability for a dimer to be a heterodimer in a correct orientation allowing for cis-splicing would be one eighth, when AAV-EF1αEP and AAV-Pless-nlsLacZ were co-delivered (Group 4). Similarly the maximum restoration of expression from AAV-(EF1αEP)$_2$ that contained an enhancer/promoter in two orientations would be one fourth (Group 5). This suggests that the β-gal restoration by cis-spliced mRNA should have been 13% and 25% in groups 4 and 5, respectively compared to that of the complete single vector (group 6).

Figure 3:
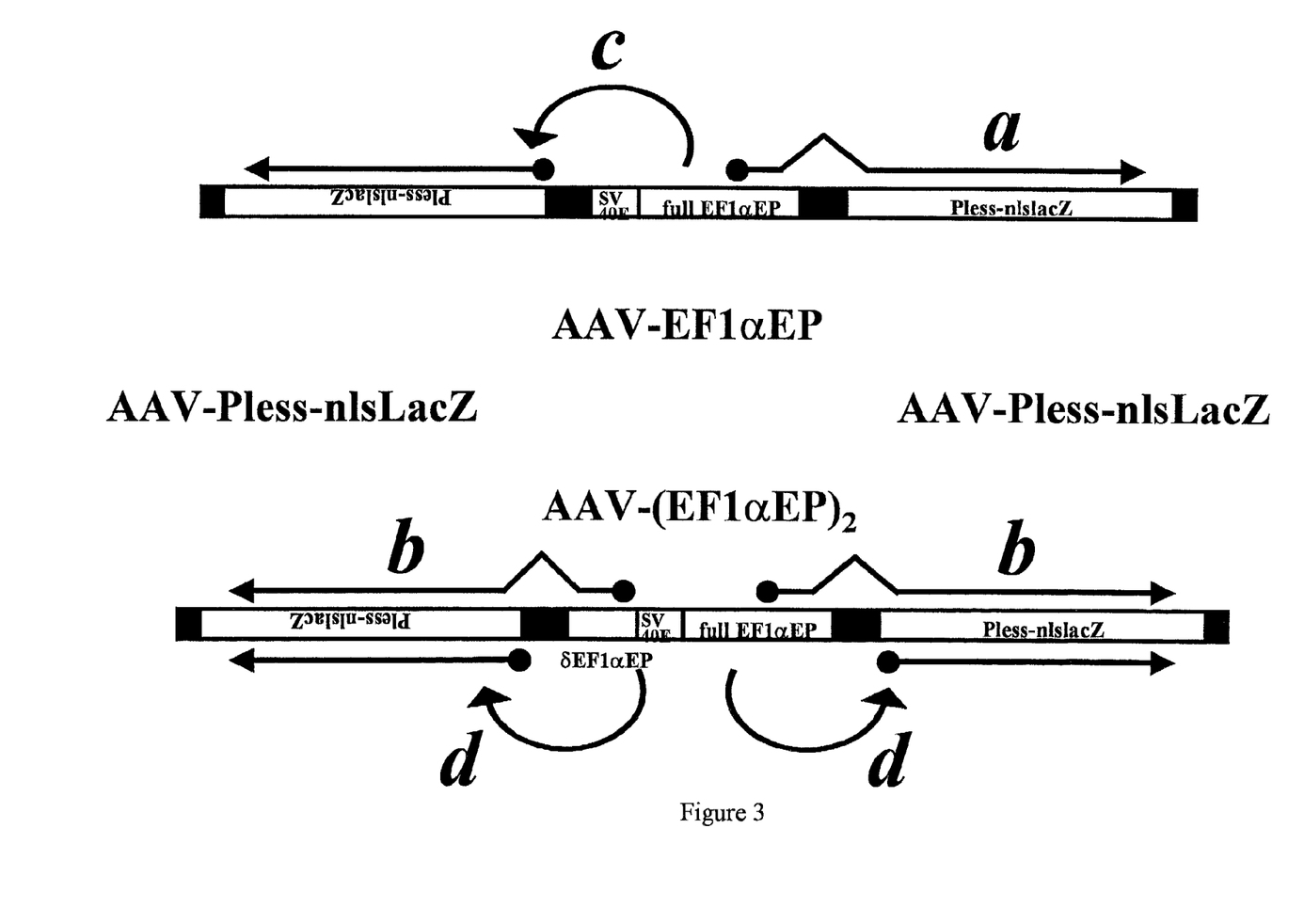
FIG. 3 provides a schematic representation of the mechanisms of in vivo enhancement of transgene expression from the AAV-Pless-nlsLacZ vector by AAV-EF1αEP or AAV-(EF1αEP)$_2$ vector of the subject invention.

The higher-than-expected β-gal expression measured by ELISA in the co-injected livers was likely due to the increase in cis-enhanced nlslacZ transcripts from AAV-Pless-nlsLacZ, presumably by orientation-independent enhancer activity of the EF1αEP(s) (see FIG. 3). This would also explain why the number of X-gal positive hepatocytes was coordinately increased.

The demonstration of cis-splicing from two complimentary rAAV vectors in hepatocytes is of great importance, because it indicates that large cDNA can be expressed by this novel rAAV vector approach. In addition, the demonstration of cis-enhancement of a slightly larger mRNA transcribed from a cryptic transcription start site in a single rAAV by a second enhancer/promoter vector, indicates that greater enhancement is achievable if an efficient promoter is incorporated upstream of a cDNA in a rAAV vector and co-delivered it with a second vector where only the cis-enhancement effect of the second enhancer vector would occur. In this case, the minimal promoter sequence without an enhancer could be used, and a relatively large cDNA could be incorporated in a single vector.

The above results demonstrate that the subject invention greatly increases the usefulness of rAAV vectors. For example, the subject rAAV vector based methods may be employed to transfer the cystic fibrosis transmembrane conductance regulator (CFTR) gene and the human coagulation factor VIII gene, both of whose cDNAs barely fit into a single rAAV vector. Furthermore, these genes could be coupled with tissue specific enhancer/promoters carried on another rAAV vector, thereby increasing the specificity of gene delivery.

It is evident from the above results and discussion that the subject invention provides for a significant improvement in rAAV vectors. Specifically, the subject invention greatly enhances the length of expression cassettes that may be delivered using rAAV vectors. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for introducing a functional expression cassette into a cell, said method comprising:
   (a) providing a population of first and second adeno-associated viral particles, wherein said first adeno-associated viral particle comprises a first portion of an expression cassette and said second adeno-associated viral particle comprises a second portion of an expression cassette; and
   (b) contacting said cell with said first and second adeno-associated viral particles under conditions sufficient for a hetero-concatemer to be produced inside said cell, wherein said hetero-concatemer comprises a functional expression cassette made up of said first and second portions separated by an intron comprising an inverted terminal repeat (ITR) sequence, wherein said contacting occurs in vitro;
   to introduce a functional expression cassette into said cell.

2. The method according to claim 1, wherein said functional expression cassette comprises DNA capable of being transcribed into an mRNA molecule.

3. The method according to claim 1, wherein said functional expression cassette is longer than about 4.7 kb.

4. The method according to claim 1, wherein said population comprises only two distinct adeno-associated viral vectors.

5. A kit for use in introducing a functional expression cassette into a cell, said kit comprising:
  first and second plasmid vectors for producing a population of at least two distinct adeno-associated viral particles, wherein each distinct member of said population of at least two distinct adeno-associated viral particles comprises a different portion of said single an expression cassette that produce a hetero-concatemer comprising a single expression cassette; and
  instructions for practicing the method according to claim 1.

6. The kit according to claim 5, wherein said first plasmid vector comprises an insertion site flanked by adeno-associated virus inverted terminal repeat (ITR) sequences.

7. The kit according to claim 5, wherein said second plasmid vector comprises Rep and Cap coding sequences.

8. The kit according to claim 5, wherein said kit further comprises a source of adenovirus helper proteins.

9. The kit according to claim 5, wherein said kit further further comprises a packaging cell line.

10. An isolated cell comprising a an adeno-associated viral hetero-concatemer, wherein said hetero-concatemer comprises a functional expression cassette, wherein said functional expression cassette comprises at least two portions of the functional expression cassette separated by an intron comprising an inverted terminal repeat (ITR) sequence.

11. The isolated cell according to claim 10, wherein said expression cassette is longer than about 4.7 kb.

12. The isolated cell according to claim 10, wherein said expression cassette comprises two portions separated by an intron comprising an ITR sequence.

13. The isolated cell according to claim 12, wherein said cell is a hepatic cell.

14. An that produce a hetero-concatemer comprising a single expression cassette adeno-associated viral vector preparation for introducing an expression cassette into a cell, comprising:
  a population of at least two distinct adeno-associated viral particles, wherein each distinct member of said population comprises a different portion of said single expression cassette.

15. The preparation according to claim 14, wherein said expression cassette is capable of being transcribed into an mRNA.

16. The preparation according to claim 14, wherein said expression cassette is longer than about 4.7 kb in length.

17. The preparation according to claim 14, wherein said preparation comprises a first population of adeno-associated viral vectors comprising a first portion of said expression cassette and a second population of viral vectors comprising a second portion of said expression cassette.

18. The preparation according to claim 14, wherein said preparation is present in a pharmaceutical delivery vehicle.

* * * * *

UNITED STATES PATENT AND TRADEMARK OFFICE
CERTIFICATE OF CORRECTION

| | |
|---|---|
| PATENT NO. | : 7,060,497 B2 |
| APPLICATION NO. | : 09/797858 |
| DATED | : June 13, 2006 |
| INVENTOR(S) | : Hiroyuki Nakai et al. |

It is certified that error appears in the above-identified patent and that said Letters Patent is hereby corrected as shown below:

In Claim 14, column 20, lines 9-10, the phrase "that produce a hetero-concatemer comprising a single expression cassette" after the word "An" and before the word "adeno-associated" should be deleted.

In Claim 14, column 20, line 14, the phrase -- that produce a hetero-concatemer comprising a single expression cassette -- should be inserted after the word "particles" and before the word "wherein".

Signed and Sealed this

Seventeenth Day of April, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,060,497 B2 | Page 1 of 1 |
| APPLICATION NO. | : 09/797858 | |
| DATED | : June 13, 2006 | |
| INVENTOR(S) | : Hiroyuki Nakai et al. | |

It is certified that error appears in the above-identified patent and that said Letters Patent is hereby corrected as shown below:

In Claim 14, column 20, lines 9-10, the phrase "that produce a hetero-concatemer comprising a single expression cassette" after the word "An" and before the word "adeno-associated" should be deleted.

In Claim 14, column 20, line 14, the phrase -- that produce a hetero-concatemer comprising a single expression cassette -- should be inserted after the word "particles" and before the word "wherein".

Signed and Sealed this

Fifteenth Day of May, 2007

JON W. DUDAS
*Director of the United States Patent and Trademark Office*